United States Patent [19]
Hasegawa et al.

[11] Patent Number: 5,166,964
[45] Date of Patent: Nov. 24, 1992

[54] METHOD AND APPARATUS FOR MEASURING DENSITY

[75] Inventors: Kenichi Hasegawa; Kuniyoshi Watanabe, both of Tokyo; Setsuro Kimura; Jun Furukawa, both of Yokohama; Kenji Akifuji, Tokyo, all of Japan

[73] Assignee: Kenichi Hasegawa & Tokimec Inc., Tokyo, Japan

[21] Appl. No.: 873,602

[22] Filed: Apr. 21, 1992

Related U.S. Application Data
[63] Continuation-in-part of Ser. No. 621,433, Dec. 4, 1990.

Foreign Application Priority Data
Dec. 12, 1989 [JP] Japan ................. 1-321909

[51] Int. Cl.$^5$ ............................................. G01B 15/02
[52] U.S. Cl. .................................. 378/89; 378/70; 378/86; 378/54; 378/55; 250/269; 250/266; 250/308
[58] Field of Search ............. 378/51, 54, 55, 56, 378/86, 89, 90.6, 70.53; 250/269, 266, 308, 253

[56] References Cited

U.S. PATENT DOCUMENTS

| | | | |
|---|---|---|---|
| 3,435,220 | 3/1969 | Hanken | 378/53 |
| 4,140,906 | 2/1979 | Morrison et al. | 378/89 |
| 4,228,351 | 10/1980 | Snow | 378/89 |
| 4,277,681 | 7/1981 | Borken | 378/54 |
| 4,539,649 | 9/1985 | Michaelis et al. | 378/53 |
| 4,641,030 | 2/1987 | Reigmand | 378/89 |
| 4,931,638 | 6/1990 | Chernyak et al. | 250/253 |
| 4,949,365 | 8/1990 | Koike et al. | 378/54 |

Primary Examiner—Constantine Hannaher
Assistant Examiner—Kim-Kwok Chu
Attorney, Agent, or Firm—Wenderoth, Lind & Ponack

[57] ABSTRACT

A distance between a radiation source and a detector is first set to a first distance and the number of pulses of a γ-ray is detected. Then, the distance between the radiation source and the detector is set to a second distance different from the first distance and the number of γ-ray pulses is detected. A density ρ of a sample is finally calculated on the basis of a ratio of the two detection pulse numbers which were detected. The radiation source is set on the surface of the sample or in the sample. The sample detector is set on the sample surface. Fundamentally, one radiation source and two detectors are used. In the case of using one radiation source and one detector, either one of them is moved and the number of pulses is detected twice.

9 Claims, 7 Drawing Sheets

FIG.1

PRIOR ART

METHOD AND APPARATUS FOR MEASURING DENSITY

This application is a continuation-in-part of now abandoned application Ser. No. 07/621,433, filed Dec. 4, 1990.

BACKGROUND OF THE INVENTION

The present invention relates to method and apparatus for measuring a density of a sample by using a γ-ray and, more particularly, to method and apparatus for measuring a density of a sample by counting the number of γ-rays which were scattered by the sample or the number of γ-ray pulses which are transmitted through the sample per unit time.

Figure 1:
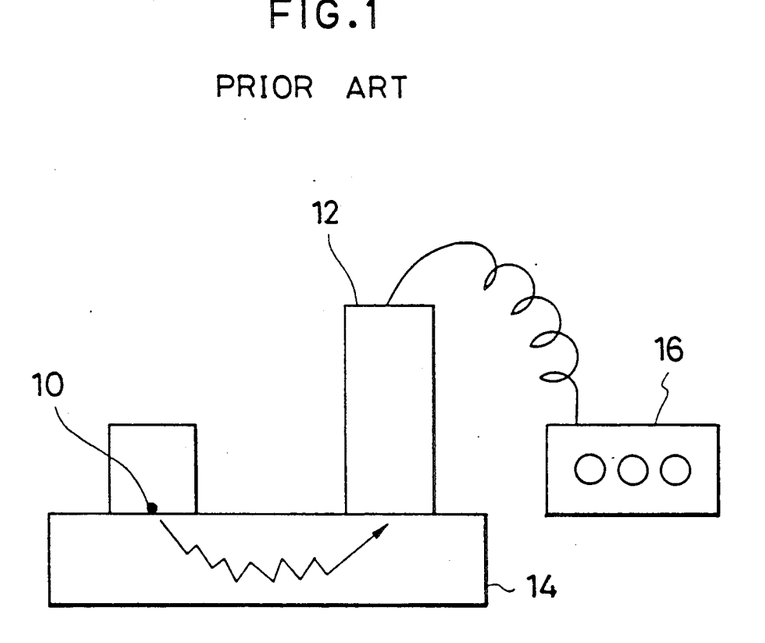
FIG. 1 is an explanatory diagram of a conventional surface scattering type densitometer.
Figure 2:
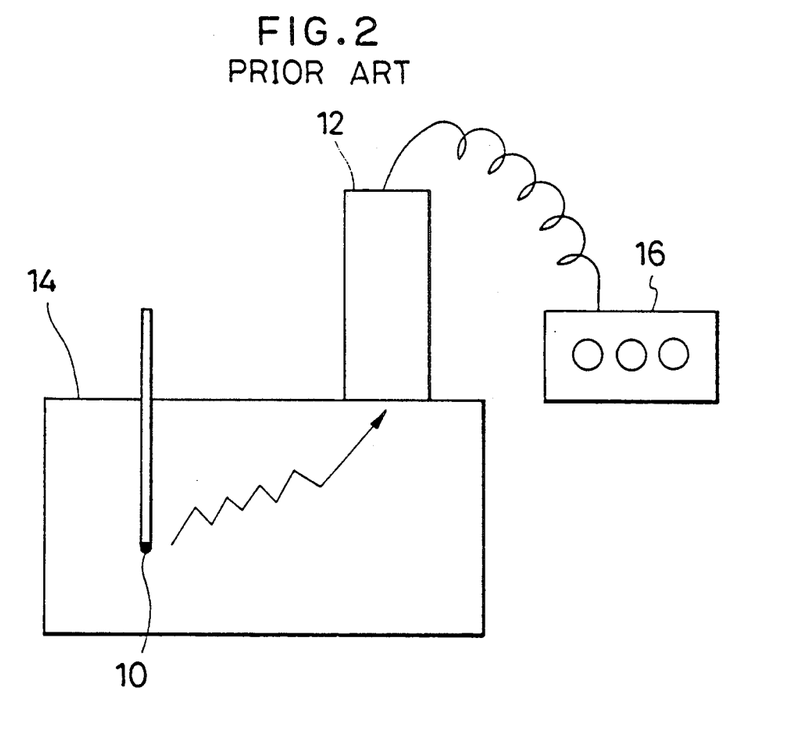
FIG. 2 is an explanatory diagram of a conventional transmitting type densitometer.

Hitherto, for instance, a surface scattering type densitometer shown in FIG. 1 or a transmitting type densitometer shown in FIG. 2 has been known as a densitometer using a γ-ray.

In the surface scattering type densitometer of FIG. 1, a radiation source 10 and a detector 12 are arranged on the surface of a sample 14 so as to be away from each other at a predetermined distance. The γ-ray pulses which are scattered in the sample and are returned to the sample surface in the γ-ray which was irradiated from the radiation source 10 are detected by the detector 12. A detection signal of the detector 12 is output to a measuring apparatus 16. The number N of detection pulses per unit time is counted by the measuring apparatus 16. A correlation curve to obtain a density ρ from the number N of detection pulses of the γ-ray shown in FIG. 3 has been preset in the measuring apparatus 16. The value of the density ρ corresponding to the pulse number N which was counted in accordance with the correlation curve is obtained and output and displayed.

In the transmitting type densitometer of FIG. 2, the radiation source 10 is arranged in the sample 14, the γ-ray pulses which are transmitted in the sample from the radiation source 10 are detected by the detector 12 attached onto the surface of the sample, and the density ρ can be obtained from the number N of detection pulses per unit time by the measuring apparatus 16 in a manner similar to the surface scattering type densitometer.

Figure 3:
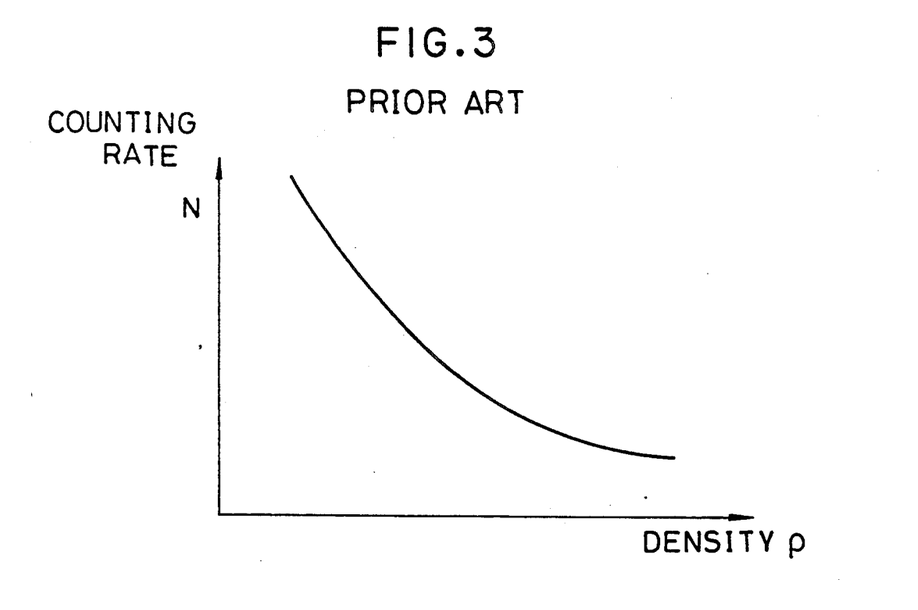
FIG. 3 is a correlation curve diagram between the count value of the $\gamma$-ray pulses and the density in a conventional apparatus.

In the conventional densitometer using the γ-ray, the correlation curve shown in FIG. 3 which is used to obtain the density ρ from the count number N of the γ-ray pulses is formed from the experimental data obtained under the ideal measuring conditions. However, in the actual measurement, the correlation between the count value N and the density ρ according to the correlation curve is not always obtained due to a change in characteristics of the measuring apparatus depending on a temperature, an influence by a half value period of the radiation source, and the like. Further, there is a problem such that the stability and reliability of the density measurement are insufficient.

SUMMARY OF THE INVENTION

It is an object of the invention to provide a density measuring method which can stably obtain an accurate measurement result without being influenced by the measuring conditions.

Another object of the invention is to provide a density measuring apparatus which can stably obtain an accurate measurement result without being influenced by the measuring conditions.

Still another object of the invention is to provide method and apparatus for measuring a density in which one radiation source and two detectors are provided.

Further another object of the invention is to provide method and apparatus for measuring a density, in which one radiation source and one detector are provided, the radiation source is moved to two positions, the number of γ-ray pulses is counted, thereby obtaining a density.

Further another object of the invention is to provide method and apparatus for measuring a density, in which one radiation source and one detector are provided, the detector is moved to two positions, the number of γ-ray pulses is counted, thereby obtaining a density.

Further another object of the invention is to provide method and apparatus for measuring a density, in which three detectors are provided for one radiation source.

Further another object of the invention is to provide method and apparatus for measuring a density, in which a plurality of radiation sources and a plurality of detectors are provided.

That is, according to the invention, there is provided a density measuring method whereby γ-ray pulses are irradiated into a sample from a radiation source, the number of γ-ray pulses which were transmitted or scattered in the sample is detected by a detector, and a density of the sample is measured on the basis of the number of detection pulses. With respect to the measuring method, according to the invention, a distance between the radiation source and the detector is set to a first distance $L_1$, the number $N_1$ of pulses of the γ-ray is detected, a distance between the radiation source and the detector is set to a second distance $L_2$ different from the first distance $L_1$, the number $N_2$ of pulses of the γ-ray is detected, and a density ρ of the sample is calculated on the basis of a ratio $(N_1/N_2)$ of the numbers $N_1$ and $N_2$ of detection pulses for the first and second distances $L_1$ and $L_2$.

On the other hand, according to the invention, there is provided a density measuring apparatus of the surface scattering type comprising: a radiation source, arranged on the surface of a sample, for irradiating a γ-ray into the sample; a first detector, arranged on the surface of the sample so as to be away from the radiation source at a first distance $L_1$, for detecting γ-ray pulses which are scattered in the sample; a second detector, arranged on the sample surface so as to be away from the radiation source at a second distance $L_2$ different from the first distance $L_1$, for detecting the γ-ray pulses which are scattered in the sample; and a measuring apparatus for counting the numbers $N_1$ and $N_2$ of pulses per unit time of the γ-ray pulses which are detected by the first and second detectors and for calculating a density ρ of the sample on the basis of a ratio $(N_1/N_2)$ of the pulse count values.

In the density measuring method and apparatus according to the invention, the density ρ is calculated on the basis of the two detection pulse numbers $N_1$ and $N_2$ from the following relational equation $$ln(N_1/N_2) = A\rho + C$$

(where, A and C are constants) as follows.

$$\rho = \{C - ln(N_1/N_2)\}/A$$

As mentioned above, according to the invention, since a density is obtained by using the ratio between the detection results of the γ-ray pulses of two systems for the same sample, a degree of influence which is exerted on the system by a change in characteristics of the measuring apparatus depending on a temperature is minimum. The stable measurement result is obtained also without being influenced by a half value period of the radiation source and a detecting efficiency of the detector.

On the other hand, since the natural logarithm of the ratio ($N_1/N_2$) of the numbers of pulses is a linear function of the density $\rho$, the relation between them is simplified and if the relation between two points is known, a correlation curve can be easily obtained.

The above and other objects, features, and advantages of the invention will become more apparent from the following detailed description in conjunction with the accompanying drawings.

DETAILED DESCRIPTION OF THE PREFERRED EMBODIMENTS

Figure 4:
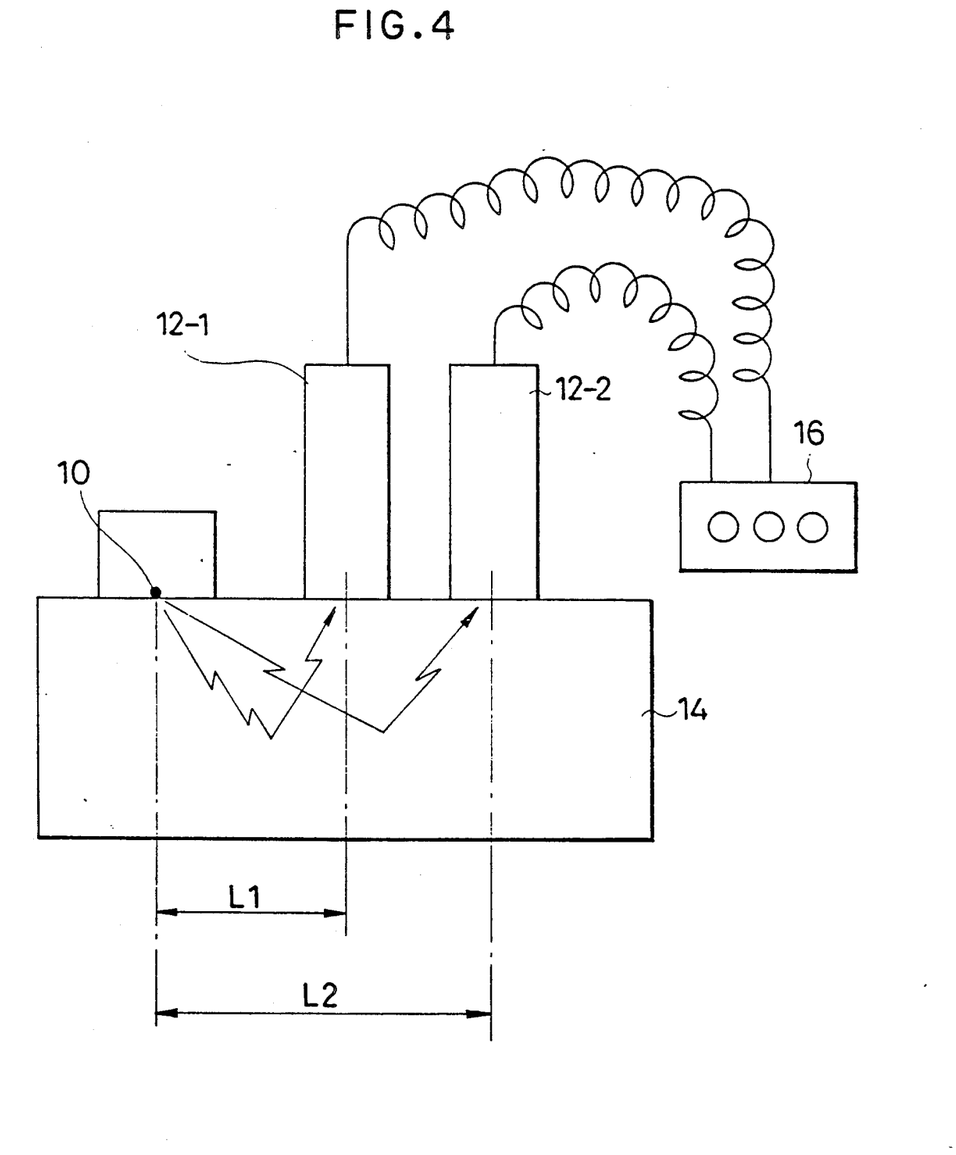
FIG. 4 is a constructional diagram showing the first embodiment of the invention.

In FIG. 4, reference numeral 10 denotes the radiation source to irradiate a $\gamma$-ray. The radiation source 10 is arranged on the surface of the sample 14 to be measured in a density measuring apparatus of the surface transmitting type and irradiates the $\gamma$-ray into the sample 14. A detector 12-1 is arranged on the surface of the sample 14 which is away from the radiation source 10 at a predetermined distance $L_1$ (first distance). A detector 12-2 is arranged on the surface of the sample 14 which is away from the radiation source 10 at a predetermined distance $L_2$ (second distance). There is the following relation between the distances $L_1$ and $L_2$ of the detectors 12-1 and 12-2 from the radiation source 10.

$$L_1 < L_2$$

The detectors 12-1 and 12-2 detect $\gamma$-ray pulses which are radiated into the sample 14 from the radiation source 10 and returned to the surface by the scattering during the passage of the sample. Detection outputs of the detectors 12-1 and 12-2 are given to the measuring apparatus 16.

The measuring apparatus 16 counts the number $N_1$ (count value) of $\gamma$-ray pulses per unit time which are obtained from the detector 12-1 and also counts the number $N_2$ (count value) of $\gamma$-ray detection pulses per unit time which are obtained from the detector 12-2. Then, a ratio ($N_1/N_2$) between the pulse count values $N_1$ and $N_2$ which were obtained from the two detectors 12-1 and 12-2 is obtained. Further, the density $\rho$ of the sample 14 is calculated from the ratio ($N_1/N_2$) in accordance with the following equation.

$$ln(N_1/N_2) = A\rho + C \qquad (1)$$

(where, A and C in the equation (1) are constants.)

Figure 5:
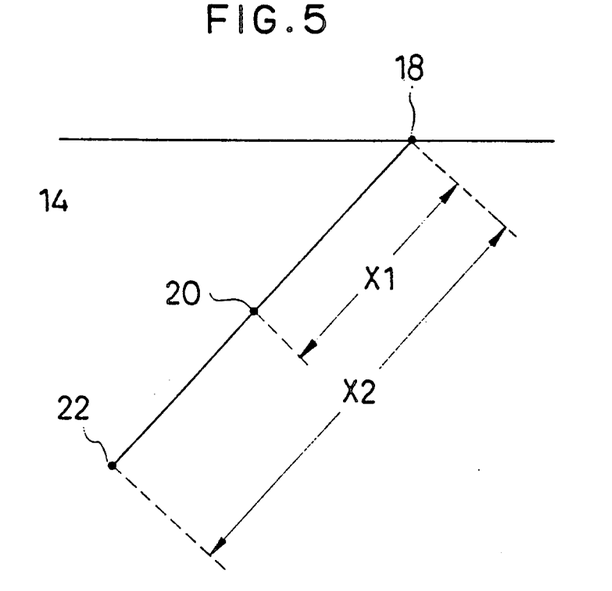
FIG. 5 is an explanatory diagram showing the measurement principle according to the invention.

Practically speaking, by modifying the equation (1), $$\rho = \{C - ln(N_1/N_2)\}/A \qquad (2)$$

the density $\rho$ is calculated. Then, the measuring principle of the density according to the invention will now be described with reference to FIG. 5.

FIG. 5 shows a state in the case where radiation sources 10-1 and 10-2 are arranged on the surface of the sample 14 at different positions on a straight line in the sample 14 for a detecting point 18 and distances from the radiation sources 10-1 and 10-2 to the detecting point 18 assume $x_1$ and $x_2$, respectively.

First, when the $\gamma$-ray passes in a material, the $\gamma$-ray is absorbed due to a photoelectric effect, a back scattering, and an interaction of an electron pair so that the intensity of the $\gamma$-ray exponentially decreases for a passing distance. Now, when it is assumed that a $\gamma$-ray having an intensity $I_0$ and a predetermined energy and an oriented direction was irradiated from the radiation source and passes through an absorber having a thickness x and that an intensity of the $\gamma$-ray after it passed through the absorber is set to I, the following relation is obtained.

$$I = I_0 B e^{-\mu x} \qquad (3)$$

(where, B is a built-up coefficient) $\mu$ in the equation (3) is called a $\gamma$-ray absorption coefficient.

On the other hand, the $\gamma$-ray absorption coefficient $\mu$ for the sample is given by a function the density $\rho$ of the sample. According to the experiments by the present inventors, it has been confirmed that the linear relation of the following equation is almost satisfied if a difference which is significant for the compositions of the sample does not exist between the $\gamma$-ray absorption coefficient $\mu$ and the density $\rho$.

$$\mu = f(\rho) = P\rho + Q \qquad (4)$$

(where, P and Q are constants)

Therefore, now assuming that the intensity of the $\gamma$-ray which is irradiated from the radiation source 10-1 in FIG. 5 is set to $I_0$, an intensity $I_1$ of the $\gamma$-ray which is obtained at the detecting point 18 after it passed through the sample 14 by the distance $x_1$ is obtained by the following equation (5) in consideration of a scattering cross sectional area or the like in FIG. 5.

$$I_1 = B_1 \cdot I_0 \cdot e^{-f(\rho)x_1} \qquad (5)$$

Similarly, with respect to the γ-ray from the radiation source 10-2, an intensity $I_2$ of the γ-ray is obtained by the following equation (6).

$$I_2 = B_2 \cdot I_0 \cdot e^{-f(\rho)x_2} \quad (6)$$

In the equations (5) and (6). $B_1$ and $B_2$ denote built-up coefficients each including a change in coefficient efficiency due to an intensity of radiation source, a detecting efficiency which is peculiar to the detector, a gap between the detector and the sample surface, and the like.

As mentioned above, according to the invention, the radiation sources 10-1 and 10-2 having the same intensity are arranged at the positions which are away from the detecting point 18 by the different distances $x_1$ and $x_2$ and the intensities $I_1$ and $I_2$ of the γ-rays which were irradiated from the radiation sources 10-1 and 10-2 and passed in the sample 14 are detected, respectively. When a natural logarithm $$\ln(I_1/I_2)$$

of the ratio between the intensities at the detecting point 18 of the γ-rays from the two radiation sources 10-1 and 10-2 which were obtained by the equations (5) and (6) is calculated, it becomes as follows.

$$\ln(I_1/I_2) = \ln(B_1/B_2) + f(\rho)(x_2 - X_1) \quad (7)$$

where, $\ln(B_1/B_2)$ in the equation (7) is a constant which is peculiar to the detecting system.

In the actual measurement of the density, the intensities $I_1$ and $I_2$ of the γ-rays at the detecting point 18 which passed in the sample by the different distances $x_1$ and $x_2$ which were obtained by the equations (5) and (6) are detected by the numbers of γ-ray pulses, that is, the count values $N_1$ and $N_2$ of γ-ray pulses which are obtained per unit time. Therefore, the following relation is satisfied.

$$\ln(I_1/I_2) = \ln(N_1/N_2) \quad (8)$$

FIG. 5 is a principle diagram in the case of the transmitting type densitometer in which a radiation source is provided in a sample. In the case of the surface scattering type densitometer shown in FIG. 4, the γ-ray which was irradiated from the radiation source into the sample is scattered in the sample and a certain degree of the γ-ray which was caused due to the scattering arrives at the detecting point. Therefore, the points corresponding to the radiation sources 10-1 and 10-2 lie within a wide range. Thus, transmission average distances which are expressed by $K_1L_1$ and $K_2L_2$ for distances $L_1$ and $L_2$ corresponding to $x_1$ and $x_2$ are used and substituted into $x_1$ and $x_2$ in the equation (7). The equation obtained by the substitution is input into the equation (8) and the density $\rho$ having a linear function relation of the equation (4) with respect to $f(\rho)$ is substituted, so that the following equation is derived.

$$\begin{aligned}
\ln(N_1/N_2) &= \ln(B_1/B_2) + (P\rho + Q)(K_2L_2 - K_1L_1) \quad (9)\\
&= (K_2L_2 - K_1L_1)P\rho + Q(K_2L_2 - K_1L_1) +\\
&\quad \ln(B_1/B_2)\\
&= A\rho + C
\end{aligned}$$

where, $A = (K_2L_2 - K_1L_1)P$
$C = Q(K_2L_2 - K_1L_1) + \ln(B_1/B_2)$

That is, the linear function relation between the natural logarithm of the ratio $(N_1/N_2)$ of the pulse count values of the equation (1) in the measuring apparatus 16 of FIG. 4 and the density $\rho$ is satisfied.

Even in the case where the radiation sources 10-1 and 10-2 having the same intensity are arranged at the positions in the sample 14 in FIG. 5 which are away from the detecting point 18 by the different distances $x_1$ and $x_2$ and the γ-rays are detected at the detecting point 18, the above detecting principle is satisfied in substantially the same manner as in the case of the surface scattering type densitometer shown in FIG. 4 except that the constants $K_1$, $K_2$, $B_1$, and $B_2$ have the fixed values which are peculiar to the transmitting type densitometer. Therefore, it is possible to consider that the density is measured by the same detecting principle.

Figure 6:
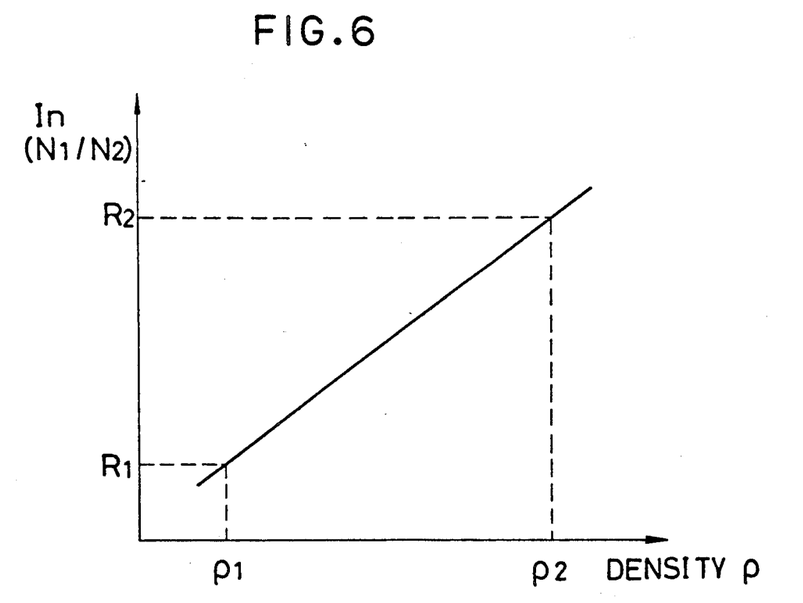
FIG. 6 is a correlation curve diagram between the natural logarithm of a ratio of pulse count values and the density according to the invention.

Consequently, a correlation curve between the natural logarithm $$\ln(N_1/N_2)$$

of the ratio of the pulse count values which is given by the equation (1) and the density $\rho$ is obtained in accordance with the measuring principle of the invention shown in FIG. 5 and is set to the measuring apparatus 16 shown in FIG. 4. Since the correlation curve has a linear relation, it obviously has a relation of a straight line as shown in FIG. 6.

Practically speaking, the correlation straight line shown in FIG. 6 is set in the following manner. Two reference samples having the same material and different densities are prepared. The radiation source 10 and two detectors 12-1 and 12-2 are provided for each of the samples as shown in FIG. 4. The count values are obtained by the measuring apparatus 16. The natural logarithms of ratios $R_1$ and $R_2$ of densities $\rho_1$ and $\rho_2$ of two count values $N_1$ and $N_2$ are obtained and are plotted on an axis of ordinate. An intersection between the natural logarithm of the ratio $R_1$ and the density $\rho_1$ and another intersection between the natural logarithm of the ratio $R_2$ and the density $\rho_2$ are obtained at two locations. A straight line which is obtained by connecting the two intersections is formed as a correlation straight line.

Figure 7:
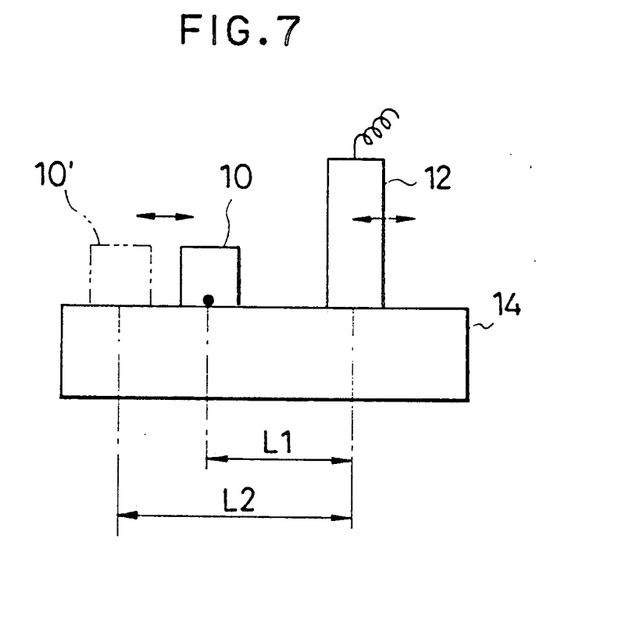
FIG. 7 is a constructional diagram showing the second embodiment of the invention.

FIG. 7 is an explanatory diagram showing the second embodiment of the invention and is characterized in that the density is measured by using only one detector.

That is, in the embodiment of FIG. 7, the radiation source 10 and the detector 12 are set on the sample 14. First, as shown in the diagram, the pulse count value $N_1$ of the γ-ray is obtained with respect to the setting distance $L_1$ of the radiation source 10 from the detector 12. Then, the radiation source 10 is moved in such a direction as to be away from the detector 12. After the radiation source 10 was moved to a position shown by reference numeral 10' by the setting distance $L_2$, the pulse count value $N_2$ of the γ-ray is similarly obtained by the detector 12. The density $\rho$ of the sample 14 is calculated from the two pulse count values $N_1$ and $N_2$ in accordance with the equation (1).

Although the radiation source 10 has been moved in FIG. 7, it is also possible to fix the radiation source 10 and to move the detector 12, thereby changing the setting distance to $L_1$ and $L_2$.

Figure 8:
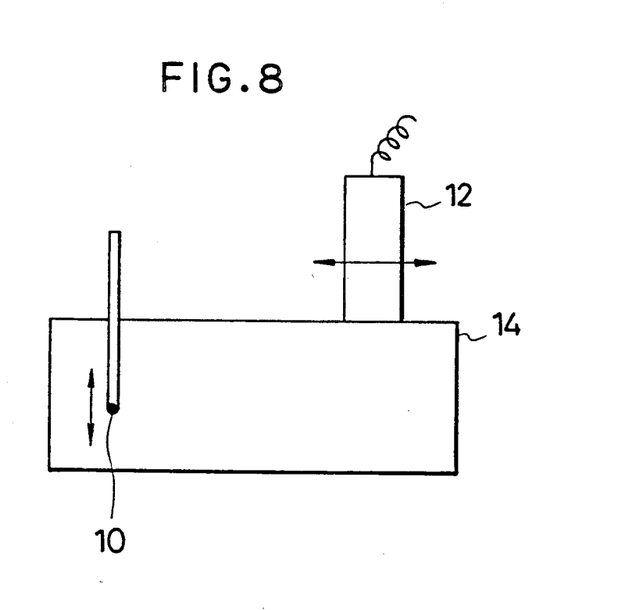
FIG. 8 is a constructional diagram showing the third embodiment of the invention.

FIG. 8 is an explanatory diagram of the third embodiment of the invention and shows an example in which a density is measured by the transmitting type densitometer in the case where a radiation source is provided in a sample.

In FIG. 8, the radiation source 10 is set in the sample 14 and the detector 12 is set on the surface of the sample 14. To realize the density measurement of the invention, for instance, the radiation source 10 is moved in the vertical direction and the pulse count values $N_1$ and $N_2$ of the γ-rays are obtained by the detector 12 at the different positions, respectively.

On the other hand, in place of moving the radiation source 10, it is also possible to construct in a manner such that the radiation source 10 is fixed and the detector 12 is moved on the surface of the sample 14 in the directions indicated by arrows and the pulse count values $N_1$ and $N_2$ of the γ-rays are obtained at different setting distances $L_1$ and $L_2$.

Figure 9:
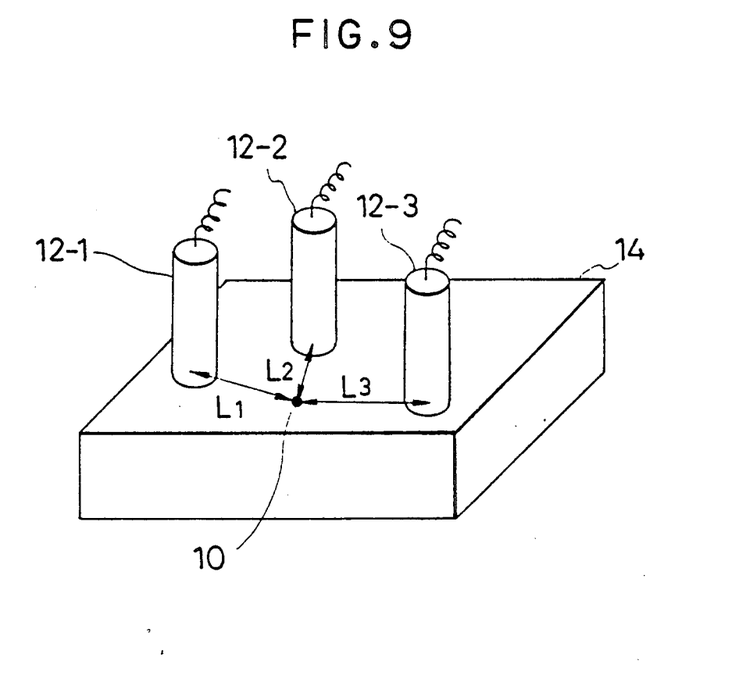
FIG. 9 is a constructional diagram showing the fourth embodiment of the invention.

FIG. 9 shows the third embodiment of the invention. In the embodiment, three detectors 12-1, 12-2, and 12-3 are arranged at different setting distances $L_1$, $L_2$, and $L_3$ so as to be away from the radiation source 10 set on the surface of the sample 14 to be measured. Therefore, a density $\rho_{12}$ is calculated from the ratio of the pulse count values $N_1$ and $N_2$ of the γ-rays which were obtained by the detectors 12-1 and 12-2. On the other hand, a density $\rho_{23}$ is similarly calculated from the pulse count values $N_2$ and $N_3$ of the γ-rays which were obtained from the detectors 12-2 and 12-3. The density can be also obtained as an average value of both of the densities $\rho_{12}$ and $\rho_{23}$ as follows.

$$\rho = (\rho_{12} + \rho_{23})/2$$

It is also possible to obtain the density from the ratios of the count values $N_1$ and $N_3$ of the detectors 12-1 and 12-3 and to calculate the average value of three calculated densities.

Figure 10:
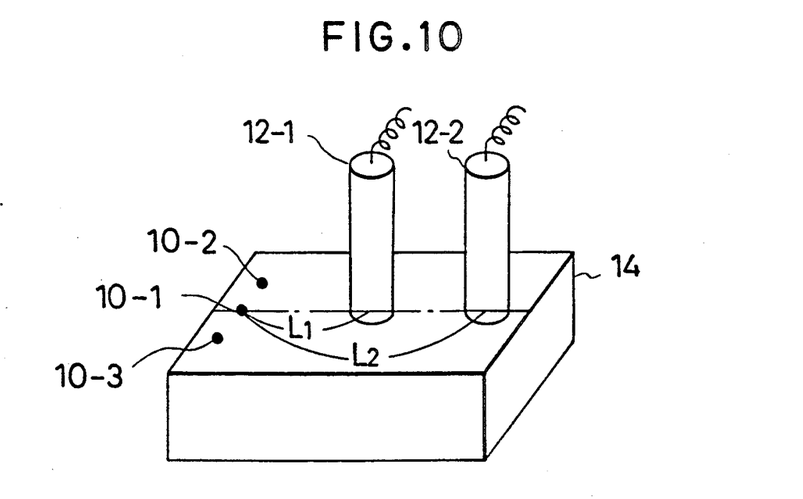
FIG. 10 is a constructional diagram showing the fifth embodiment of the invention.

FIG. 10 shows the fourth embodiment of the invention. Two detectors 12-1 and 12-2 are fixedly set on the surface of the sample 14 so as to be away from the radiation source 10-1 by different setting distances $L_1$ and $L_2$. For instance, two other radiation sources 10-2 and 10-3 are provided on both sides of the radiation source 10-1. The radiation sources 10-1, 10-2, and 10-3 are set on the surface of the sample 14 in accordance with this order. Three densities $\rho$ are obtained from the γ-ray pulse count values $N_1$ and $N_2$ of the detectors 12-1 and 12-2 for the respective radiation sources. For example, the final density is obtained as an average value of the three densities.

Figure 11:
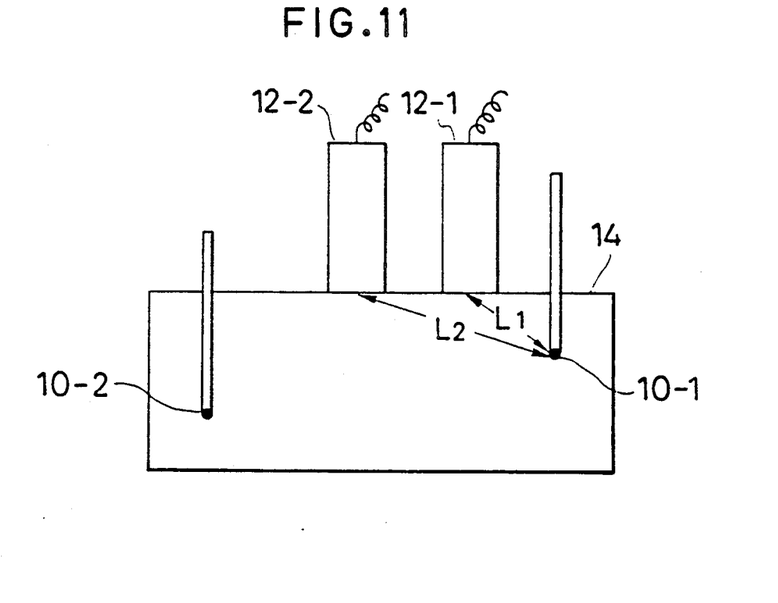
FIG. 11 is a constructional diagram showing the sixth embodiment of the invention.

FIG. 11 shows the fifth embodiment of the invention. A measuring method using a plurality of radiation sources was applied to the transmitting type densitometer in which radiation source is provided in a sample in a manner similar to the embodiment of FIG. 10. That is, the radiation sources 10-1 and 10-2 can be set at different positions in the sample 14. Two detectors 12-1 and 12-2 are set on the surface of the sample 14. First, only the radiation source 10-1 is set and the density $\rho$ is calculated from the γ-ray pulse count values $N_1$ and $N_2$ which are obtained from the detectors 12-1 and 12-2 at this time. Subsequently, only the radiation source 10-2 is set, the γ-ray pulse count values $N_1$ and $N_2$ are obtained from the detectors 12-1 and 12-2, and the density $\rho$ is similarly calculated. The measurement value is finally taken out as an average of the two densities calculated. In FIG. 11, it is also obviously possible to measure the density by using the transmitting type densitometer in which only either one of the radiation sources 10-1 and 10-2 is provided.

Figure 12:
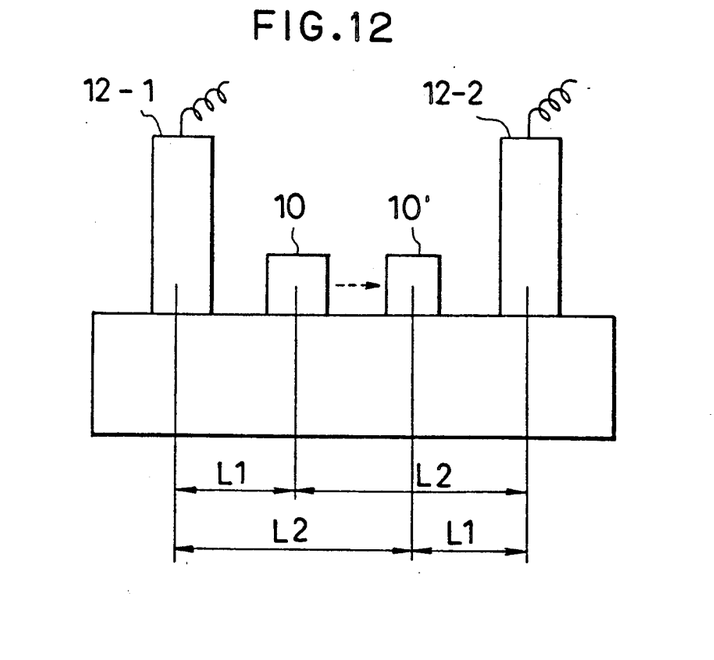
FIG. 12 is a constructional diagram showing the seventh embodiment of the invention.

FIG. 12 shows the sixth embodiment in which a measuring time can be reduced into ½ of that in the case of using the measuring method of FIG. 7. The radiation source 10 is first set at a position shown in FIG. 12 and data corresponding to the setting distances $L_1$ and $L_2$ are obtained by the detectors 12-1 and 12-2. Further, the radiation source 10 is moved to the position indicated by reference numeral 10'. The data corresponding to $L_2$ is obtained by the detector 12-1. The data corresponding to $L_1$ is obtained by the detector 12-2. If the density is calculated from the results of the measurements of two times, even if the characteristics such as detecting efficiencies or the like of the detectors 12-1 and 12-2 differ, the difference is averaged and the same result as that which is obtained by measuring by using the detectors having the same characteristics is derived. On the other hand, the measuring time can be reduced into ½ of that in the case of individually measuring the detection values corresponding to $L_1$ and $L_2$ by using the single detector shown in FIG. 4.

Further, the density obtained at the first time assumes $\rho_1$ and the density obtained at the second time assumes $\rho_2$. In the case of applying the equation (9) to calculate the densities $\rho_1$ and $\rho_2$, by calculating the weighted mean of those densities, a variation in counting efficiencies of the detectors 12-1 and 12-2 is eliminated and the true density $\rho$ of the sample can be obtained.

That is, when it is assumed at the first time that the distance between the radiation source 10 and the detector 12-1 is set to $L_1$ and the distance between the radiation source 10 and the detector 12-2 is set to $L_2$, the count value of the detector 12-1 assumes $N_{11}$ and the count value of the detector 12-2 assumes $N_{12}$. When it is assumed at the second time that the distance between the radiation source 10' and the detector 12-1 is set to $L_2$ and the distance between the radiation source 10' and the detector 12-2 is set to $L_1$, the count value of the detector 12-1 assumes $N_{22}$ and the count value of the detector 12-2 assumes $N_{21}$. Further, when assuming that the counting efficiency of the detector 12-1 is set to $E_1$ and the counting efficiency of the detector 12-2 is set to $E_2$, the arithmetical mean $(\rho_1 + \rho_2)/2$ is obtained by the following relational equation.

$$\begin{aligned}\rho &= (\rho_1 + \rho_2)/2 \\ &= \frac{\ln(N_{11} \cdot E_1/N_{12} \cdot E_2) + \ln(N_{21} \cdot E_2/N_{22} \cdot E_1) - 2 \cdot C}{2 \cdot A} \\ &= \frac{\ln(N_{11} \cdot N_{21}/N_{12} \cdot N_{22})}{2 \cdot A} - C\end{aligned}$$

The counting efficiencies $E_1$ and $E_2$ of the detectors 12-1 and 12-2 are set off. The constants A and C are peculiar constants which the measuring apparatus itself previously has. The constant A and C are constants which have already been known at the time of calibration or adjustment before the density of the sample is measured. Therefore, the true density $\rho$ of the sample can be obtained without being influenced by a variation in counting efficiencies of the detectors 12-1 and 12-2.

In the measuring method shown in FIG. 12, a measuring method which can further improve the accuracy will now be described.

First, the distance between the radiation source 10 and the detector 12-1 assumes $L_1$ and the distance between the radiation source 10 and the detector 12-2 assumes $L_2$. The number of γ-ray pulses which have passed in the sample is counted by the detectors 12-1 and 12-2, thereby obtaining the count value $N_{11}$ of the detector 12-1 and the count value $N_{12}$ of the detector 12-2.

By subsequently moving the radiation source 10 to the position shown by reference numeral 10′, the distance between the radiation source 10′ and the detector 12-1 is set to $L_2$ and the distance between the radiation source 10′ and the detector 12-2 is set to $L_1$. The number of γ-ray pulses which have passed in the sample is counted by the detectors 12-1 and 12-2, thereby obtaining the count value $N_{22}$ of the detector 12-1 and the count value $N_{21}$ of the detector 12-2.

The count ratio ($N_1/N_2$) is calculated by executing the root mean square calculation of the following equation on the basis of the count values $N_{11}$, $N_{12}$, $N_{22}$, and $N_{21}$.

$$N_1/N_2 = \sqrt{N_{11} \cdot N_{21}/N_{12} \cdot N_{22}}$$

The density ρ of the sample is obtained on the basis of the count ratio ($N_1/N_2$).

According to the above density measuring method, even when there is a variation in counting efficiencies of the detectors 12-1 and 12-2, by executing the square mean calculation, the variation in the counting efficiencies of the detectors 12-1 and 12-2 is set off. Thus, the true density ρ of the sample can be obtained.

That is, assuming that the counting efficiency of the detector 12-1 is set to $E_1$ and the counting efficiency of the detector 12-2 is set to $E_2$, the actual count ratio ($N_1/N_2$) by the above calculation is obtained by the following relation equation.

$$N_1/N_2 = \sqrt{N_{11} \cdot E_1 \cdot N_{21} \cdot E_2/N_{12} \cdot E_2 \cdot N_{22} \cdot E_1}$$
$$= \sqrt{N_{11} \cdot N_{21}/N_{12} \cdot N_{22}}$$

In the above calculation, the counting efficiencies $E_1$ and $E_2$ in the denominator and the numerator are erased, so that the count ratio is not influenced by the count errors of the detectors 12-1 and 12-2. Consequently, even in the density calculation by the root mean square calculation, an effect similar to that in the density calculation by the arithmetical mean calculation is derived.

As mentioned above, according to the density measuring method and apparatus of the invention, since the density is obtained by using the ratio of the detection results of the γ-ray pulses of two systems for the same sample, the measurement result is not influenced by the half value period of the radiation source, detecting efficiency of the detector, and the like. A change in characteristics of the measuring apparatus depending on a temperature at the time of the measurement is cancelled. The measurement result with a high reliability can be stably obtained.

Further, since the natural logarithm of the ratio of the detection results of the γ-ray pulses of two systems, that is, the ratio ($N_1/N_2$) of the two pulse count values is expressed by a linear function of the density ρ, the relation between the natural logarithm and the density is simplified. If the relation between two points is known, a correlation curve to obtain the density can be easily obtained from the measured ratio.

What is claimed is:

1. A method of measuring a density, comprising the steps of:
    setting one radiation source to radiate γ-ray pulses onto the surface of a sample to be measured;
    setting first and second detectors onto the surface of said sample so as to be away from the radiation source by different distances;
    counting the number of γ-ray pulses which have passed in the sample by the first and second detectors;
    calculating a first density on the basis of a ratio of a count value obtained by the first detector and a count value obtained by the second detector;
    setting the distance of the first detector to the radiation source and the distance of the second detector to the radiation source into different distances by changing the position of the radiation source;
    counting the numbers of γ-ray pulses which have passed in the sample by the first and second detectors;
    calculating a second density on the basis of a ratio of a count value obtained by the first detector and a count value obtained by the second detector; and
    finally setting a mean value of the first and second densities into a density of the measuring sample.

2. A method of measuring a density, comprising the steps of:
    setting one radiation source to radiate γ-ray pulses onto the surface of a sample to be measured;
    setting first, second, and third detectors onto the surface of said sample so as to be away from the radiation source by different distances;
    counting the number of γ-ray pulses which have passed in the sample by a first, second, and third detectors;
    calculating a first density on the basis of a ratio of a count value obtained by the first detector and a count value obtained by the second detector;
    calculating a second density on the basis of a ratio of a count value obtained by the second detector and a count value obtained by the third detector; and
    finally setting a mean value of the first and second densities into a density of the sample.

3. A method of measuring a density, comprising the steps of:
    setting one radiation source to radiate γ-ray pulses onto the surface of a sample to be measured;
    setting first, second, and third detectors onto the surface of said sample so as to be away from the radiation source by different distances $L_1$, $L_2$, and $L_3$;
    counting the number of γ-ray pulses which have passed in the sample by the first, second, and third detectors;
    calculating a first density on the basis of a ratio of a count value obtained by the first detector and a count value obtained by the second detector;
    calculating a second density on the basis of a ratio of a count value obtained by the second detector and a count value obtained by the third detector;
    calculating a third density on the basis of a ratio of a count value obtained by the first detector and a count value obtained by the third detector; and finally setting a mean value of the first to third densities into a density of the sample.

4. A method of measuring a density, comprising the steps of:

setting a first radiation source to radiate γ-ray pulses onto the surface of a sample to be measured;

setting first and second detectors onto the surface of said sample so as to be away from the radiation source by different distances;

counting the number of γ-ray pulses which have passed in the sample by the first and second detectors;

calculating a first density on the basis of a ratio of a count value obtained by the first detector and a count value obtained by the second detector;

subsequently removing the first radiation source;

setting a second radiation source at a position different from the position of said first radiation source;

setting distances of the first and second detectors to the second radiation source to different distances, respectively;

counting the number of γ-ray pulses which have passed in the sample by the first and second detectors;

calculating a second density on the basis of a ratio of a count value obtained by the first detector and a count value obtained by the second detector; and finally setting a mean value of the first and second densities to a density of the sample.

5. A method of measuring a density, comprising the steps of:

setting a first radiation source to radiate γ-ray pulses onto the surface of a sample to be measured;

setting first, second, and third detectors onto the surface of the sample so as to be away from the first radiation source by different distances;

counting the number of γ-ray pulses which have passed in said sample by the first and second detectors;

calculating a first density on the basis of a ratio of a count value obtained by the first detector and a count value obtained by the second detector;

subsequently removing the first radiation source;

setting a second radiation source at a position different from the position of said first radiation source;

setting distances of the second and third detectors to the second radiation source to different distances, respectively;

counting the number of γ-ray pulses which have passed in the sample by the second and third detectors;

calculating a second density on the basis of a ratio of a count value obtained by the second detector and a count value obtained by the third detector;

subsequently removing the second radiation source;

setting a third radiation source at a position different from the positions of the first and second radiation sources;

setting distances of the first and third detectors to the third radiation source to different distances, respectively;

counting the number of γ-ray pulses which have passed in the sample by the first and third detectors;

calculating a third density on the basis of a ratio of a count value obtained by the third detector and a count value obtained by the first detector; and finally setting a mean value of the first to third densities to a density of the sample.

6. A method of measuring a density, comprising the steps of:

setting a first radiation source to radiate γ-ray pulses into a sample to be measured;

setting first and second detectors onto the surface of the sample so as to be away from the first radiation source by different distances;

counting the number of γ-ray pulses which have passed in the sample by the first and second detectors;

calculating a first density on the basis of a ratio of a count value obtained by the first detector and a count value obtained by the second detector;

subsequently removing the first radiation source;

setting a second radiation source at a different position in the sample;

setting distances $L_1$ and $L_2$ of the first and second detectors to the second radiation source to different distances, respectively;

counting the number of γ-ray pulses which have passed in the sample by the first and second detectors;

calculating a second density on the basis of a ratio of a count value obtained by the first detector and a count value obtained by the second detector; and finally setting a mean value of the first and second densities to a density of the sample.

7. A method according to any one of claims 1 to 6, wherein assuming that a ratio of the count values of two detectors is K, then the density is calculated on the basis of the following equation:

$$ln([N_1/N_2]K) = A \cdot \rho + C$$

wherein, A and C are constants and $\rho$ is a density.

8. A method of measuring a density, comprising the steps of:

setting one radiation source to radiate γ-ray pulses onto the surface of a sample to be measured;

setting first and second detectors onto the surface of the sample so as to be away from the radiation source by different distances;

counting the number of γ-ray pulses which have passed in the sample by the first and second detectors, thereby obtaining count values $N_{11}$ and $N_{12}$ of the first and second detectors, respectively;

subsequently setting distances of the first and second detectors to the radiation source to different distances, respectively, by changing the position of the radiation source;

counting the number of γ-ray pulses which have passed in the sample by the first and second detectors, thereby obtaining count values $N_{21}$ and $N_{22}$ of the first and second detectors, respectively;

obtaining a count ratio $(N_1/N_2)$ by a root mean square operation based on said count values in accordance with the following relational equation $$N_1/N_2 = \sqrt{(N_{11} \cdot N_{21})/(N_{12} \cdot N_{22})};$$ and finally calculating a density of the sample on the basis of said count ratio $(N_1/N_2)$.

9. A method according to claim 8, wherein the density of the sample is calculated on the basis of the following equation:

$$ln(N_1/N_2) = A \cdot \rho + C$$

wherein, A and C are constants and $\rho$ is a density.

* * * * *